United States Patent
Birch et al.

(10) Patent No.: US 6,201,004 B1
(45) Date of Patent: Mar. 13, 2001

(54) DIOXINO DERIVATIVES AND THEIR USE AS THERAPEUTIC AGENTS

(75) Inventors: Alan Martin Birch; Paul Anthony Bradley, both of Nottingham (GB)

(73) Assignee: Knoll Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/380,375

(22) PCT Filed: Feb. 19, 1998

(86) PCT No.: PCT/EP98/00946

§ 371 Date: Sep. 1, 1999

§ 102(e) Date: Sep. 1, 1999

(87) PCT Pub. No.: WO98/40386

PCT Pub. Date: Sep. 17, 1998

(30) Foreign Application Priority Data

Mar. 11, 1997 (GB) .................................. 9704948

(51) Int. Cl.[7] ........................ A61K 31/40; A61K 31/445; A61K 31/38; C07D 491/00; C07D 401/00
(52) U.S. Cl. ....................... 514/411; 514/321; 514/443; 514/454; 548/430; 546/198; 546/197; 549/43; 549/359
(58) Field of Search .................... 546/197, 198; 514/321, 411, 443, 454; 548/430; 549/43, 359

(56) References Cited

U.S. PATENT DOCUMENTS

| | | | |
|---|---|---|---|
| 5,302,599 | * 4/1994 | Ennis et al. | 514/278 |
| 5,593,997 | 1/1997 | Dow et al. | 514/258 |
| 5,639,757 | 6/1997 | Dow et al. | 514/261 |
| 5,665,721 | 9/1997 | Bhagwat et al. | 514/253 |
| 5,834,469 | 11/1998 | Elliott et al. | 514/249 |
| 6,107,310 | * 8/2000 | Birch et al. | 514/318 |

FOREIGN PATENT DOCUMENTS

| | | |
|---|---|---|
| 771800 | 5/1997 | (EP) . |
| 91/13872 | 9/1991 | (WO) . |
| 95/07274 | 3/1995 | (WO) . |
| 96/10028 | 4/1996 | (WO) . |
| 96/40686 | 12/1996 | (WO) . |
| 97/28161 | 8/1997 | (WO) . |
| 97/32879 | 9/1997 | (WO) . |
| 97/34895 | 9/1997 | (WO) . |

OTHER PUBLICATIONS

Hanke et al., *J. of Biol. Chem.*, 271(2), Jan. 1996, 695–701.
Ennis et al., *J. Med. Chem.*, vol. 35, 1991, 3058–66.

* cited by examiner

*Primary Examiner*—Deborah C. Lambkin
(74) *Attorney, Agent, or Firm*—Keil & Weinkauf

(57) ABSTRACT

Compounds of formula I

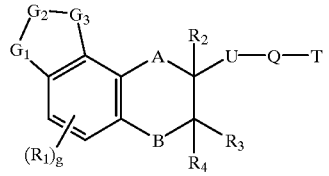

and pharmaceutically acceptable salts thereof in which A is methylene or —O—; B is methylene or —O—; $G_1$—$G_2$—$G_3$ form a heteroaromatic or heteroaliphatic chain; g is 0, 1 or 2; U is an alkylene chain optionally substituted by one or more alkyl; Q represents a divalent group containing nitrogen atoms; and T is an optionally substituted aryl or heteroaryl group, have utility in the treatment of central nervous system disorders, for example depression, anxiety, psychoses (for example schizophrenia), tardive dyskinesia, Parkinson's disease, obesity, hypertension, Tourette's syndrome, sexual dysfunction, drug addiction, drug abuse, cognitive disorders, Alzheimer's disease, senile dementia, obsessive-compulsive behavior, panic attacks, social phobias, eating disorders and anorexia, cardiovascular and cerebrovascular disorders, non-insulin dependent diabetes mellitus, hyperglycaemia, constipation, arrhythmia, disorders of the neuroendocrine system, stress, and spasticity.

21 Claims, No Drawings

DIOXINO DERIVATIVES AND THEIR USE AS THERAPEUTIC AGENTS

This appln is a 371 of PCT/EP98/00946 Feb. 19, 1998.

The present invention relates to novel dioxinoindole and thienobenzodioxin compounds which have affinity for 5-HT$_{1A}$ and/or D$_2$-like (D$_2$, D$_3$ and/or D$_4$ sub-types) receptors, to processes for their preparation, to pharmaceutical compositions containing them and to their use in the treatment of central nervous system disorders, for example depression, anxiety, psychoses (for example schizophrenia), tardive dyskinesia, Parkinson's disease, obesity, hypertension, Tourette's syndrome, sexual dysfunction, drug addiction, drug abuse, cognitive disorders, Alzheimer's disease, senile dementia, obsessive-compulsive behaviour, panic attacks, social phobias, eating disorders and anorexia, cardiovascular and cerebrovascular disorders, non-insulin dependent diabetes mellitus, hyperglycaemia, constipation, arrhythmia, disorders of the neuroendocrine system, stress, and spasticity.

WO9507274 discloses compounds of the general formula

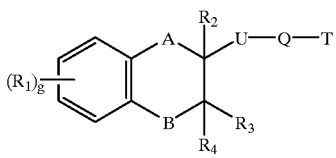

in which R$_1$ is selected from a number of substituents or two adjacent R$_1$ groups together with the carbon atoms to which they are attached form a fused benz ring, A and B are —O— or methylene, U is an alkylene chain, Q is selected from the following:

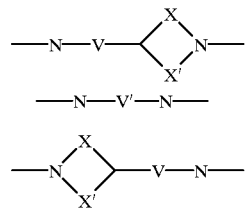

and T is an optionally substituted aromatic group optionally containing one or more N atoms. These compounds are described as being useful in the treatment of central nervous system disorders.

The present invention provides compounds of formula I

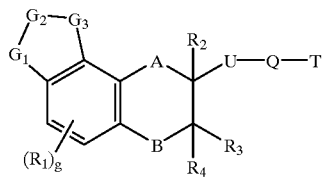

including pharmaceutically acceptable salts thereof in the form of individual enantiomers, racemates, or other mixtures of enantiomers, in which A is methylene or —O—;

B is methylene or —O—;

G$_1$—G$_2$—G$_3$ represent —N(R')—C(R")=N—, —N=C(R")—N(R')—, —N(R')—C(R")=C(R''')—, —C(R''')=C(R")—N(R')—, —N(R')—N=C(R")—, —C(R")=N—N(R')—, —N(R')—N=N—, —N=N—N(R')—, —N=C(R")—O—, —N=C(R")—S—, —O—C(R")=N—, —S—C(R")=N—, —O—N=C(R")—, —S—N=C(R")—, —C(R")=N—O—, —C(R")=N—S—, —S—C(R")=C(R''')—, —C(R")=C(R''')—S—, —O—C(R")=C(R''')—, —C(R")=C(R''')—O— or —O—C(R')(R')—O— wherein R' is H or an alkyl group containing 1 to 3 carbon atoms; and R" and R''', which are the same or different, are H; halo; an alkyl group containing 1 to 3 carbon atoms optionally substituted by one or more halo; carboxy; an alkanoyl group containing 1 to 6 carbon atoms; an alkoxycarbonyl group in which the alkoxy group contains 1 to 3 carbon atoms; formyl; cyano; or a carbamoyl group or carbamoylmethyl group each optionally N-substituted by one or two alkyl groups, which may be the same or different, each containing 1 to 3 carbon atoms;

g is 0, 1 or 2;

R$_1$ represents an alkyl group containing 1 to 3 carbon atoms optionally substituted by one or more halo; an alkoxy group containing 1 to 3 carbon atoms optionally substituted by one or more halo; halo; or an alkylthio group containing 1 to 3 carbon atoms optionally substituted by one or more halo; the substituents represented by R$_1$ being the same or different when g is 2;

R$_2$ is H or an alkyl group containing 1 to 3 carbon atoms;

R$_3$ and R$_4$, which are the same or different, are H, or an alkyl group containing 1 to 3 carbon atoms;

U is an alkylene chain containing 1 to 3 carbon atoms, optionally substituted by one or more alkyl groups each containing 1 to 3 carbon atoms;

Q represents a divalent group of formula IIa, IIb or IIc

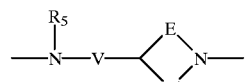

IIa

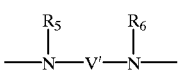

IIb

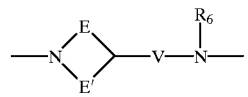

IIc in which V is (CH$_2$)$_n$, wherein n is 0, 1, 2 or 3, optionally substituted by one or more alkyl groups each containing 1 to 3 carbon atoms;

V' is an alkylene chain containing 2 to 6 carbon atoms, optionally substituted by one or more alkyl groups each containing 1 to 3 carbon atoms;

E is an alkylene chain containing 0 to 2 carbon atoms and E' is an alkylene chain containing 1 to 4 carbon atoms provided that the total number of carbon atoms in E and E' amounts to 3 or 4; and R$_5$ and R$_6$, which may be the same or different, are H or an alkyl group containing 1 to 4 carbon atoms; and T represents phenyl, 1- or 2-naphthyl, 1-naphth[2,1-d][1,2,3]oxadiazolyl, 2-, 3- or 4-pyridyl, 2-, 4- or 5-pyrimidinyl, 2- or 3-thienyl, 2- or 3-furyl, 2- 3- or 7-benzo[b]furanyl, 2,3-dihydro-7-benzo[b]furanyl, 2-, 3- or 7-benzo[b]thiophenyl, 3-, 4- or 5-pyrazolyl, 1,2,3-triazol-4-yl, 1,2,3-triazol-5-yl, 1,2,4-triazol-2-yl, 5-tetrazolyl, 2- 3- or 4-quinolinyl, 2- or 4-quinazolinyl, 3-, 4- or 5-isoxazolyl, 2-, 4- or 5-oxazolyl, 3- 4- or 5-isothiazolyl or 2-, 4- or 5-thiazolyl each of which may be optionally substituted by one or more substituents selected from a) halo, b) an alkyl group containing 1 to 4 carbon atoms optionally substituted by one or more halo, c) an alkoxy group containing 1 to 3 carbon atoms optionally substituted by one or more halo, d) an alkylthio group containing 1 to 3 carbon atoms optionally substituted by one or more halo, e) hydroxy, f) an acyloxy group containing 1 to 3 carbon atoms, g) hydroxymethyl, h) cyano, i) an alkanoyl group containing 1 to 6 carbon atoms, j) an alkoxycarbonyl group containing 2 to 6 carbon atoms, k) a carbamoyl group or carbamoylmethyl group each optionally N-substituted by one or two alkyl groups each containing 1 to 3 carbon atoms, l) a sulphamoyl or sulphamoylmethyl group each optionally N-substituted by one or two alkyl groups each containing 1 to 3 carbon atoms, m) an amino group optionally substituted by one or two alkyl groups each containing 1 to 5 carbon atoms, n) 1-pyrrolidinyl or 1-piperidinyl, o) nitro or p) acetamido.

In preferred compounds of formula I, A is —O—.

In preferred compounds of formula I, B is —O—.

In more preferred compounds of formula I, both A and B are —O—.

In preferred compounds of formula I, g is 0 or 1. When g is 1, $R_1$ is preferably halo or an alkyl group containing 1 to 3 carbon atoms. In more preferred compounds of formula I, g is 0.

In preferred compounds of formula I, $G_1$—$G_2$—$G_3$ are —N(R')—C(R")=C(R'")—; —S—C(R")=C(R'")—, —N(R')—N=C(R")—, —O—C(R")=C(R'")—, or —O—C(R')(R')—O—. Preferably, R' is H, R" is H or alkoxycarbonyl (more preferably H or ethoxycarbonyl), and R'" is H or halo (more preferably H or chloro). In more preferred compounds of formula I, $G_1$—$G_2$—$G_3$ are —O—C(R")=C(R'")— and R" and R'" are both H.

In preferred compounds of formula I, $R_2$ is H.

In preferred compounds of formula I, $R_3$ and $R_4$, are both H.

In preferred compounds of formula I, U is methylene.

In preferred compounds of formula I, Q is a group of formula IIa in which V is methylene, E and E' are both ethylene and $R_5$ is H.

In preferred compounds of formula I, T is phenyl or naphthyl, each of which may be optionally substituted by one or more substituents selected from an alkoxy group containing 1 to 3 carbon atoms, hydroxy, or halo (more preferably the substituent is methoxy). In more preferred compounds of formula I, T is phenyl optionally substituted by one or more substituents selected from an alkoxy group containing 1 to 3 carbon atoms, hydroxy, or halo (more preferably the substituent is methoxy). In especially preferred compounds of formula I, T is 2-methoxyphenyl or 2-hydroxyphenyl.

In one group of preferred compounds of formula I, both A and B are —O—; g is 0, $G_1$—$G_2$—$G_3$ are —NH—CH=CH—; —NH—C(CO$_2$C$_2$H$_5$)=CH—; —S—CH=CH—; S—CH=C(Cl)—; —NH—N=CH—; —O—CH=CH—; or —O—CH$_2$—O—; $R_2$ is H; $R_3$ and $R_4$ are both H; U is methylene; Q is a group of formula IIa in which V is methylene, E and E' are both ethylene and $R_5$ is H; and T is phenyl optionally substituted by hydroxy or by one or more alkoxy groups each containing 1 to 3 carbon atoms. More preferably, $G_1$—$G_2$—$G_3$ are —S—CH=CH— or —O—CH=CH—. Most preferably $G_1$—$G_2$—$G_3$ are —O—CH=CH—.

In another group of preferred compounds of formula I, both A and B are —O—; g is 0; $G_1$—$G_2$—$G_3$ are —N(R')—C(R")=C(R'")— wherein R' is H, R" is H or alkoxycarbonyl in which the alkoxy group contains 1 to 3 carbon atoms, and R'" is H or halo; $R_2$, $R_3$ and $R_4$ are each H; U is methylene; Q is a group of formula IIa in which V is methylene, E and E' are both ethylene and $R_5$ is H; and T is phenyl optionally substituted by hydroxy or one or more alkoxy groups.

In another group of preferred compounds of formula I, both A and B are —O—; g s 0; $G_1$—$G_2$—$G_3$ are —S—C(R")=C(R'")— wherein R" is H or alkoxycarbonyl in which the alkoxy group contains 1 to 3 carbon atoms, and R'" is H or halo; $R_2$, $R_3$ and $R_4$ are each H; U is methylene; Q is a group of formula IIa in which V is methylene, E and E' are both ethylene and $R_5$ is H; and T is phenyl optionally substituted by hydroxy or one or more alkoxy groups.

In another group of preferred compounds of formula I, both A and B are —O—; g is 0; $G_1$—$G_2$—$G_3$ are —O—C(R")=C(R'")— wherein R" is H or alkoxycarbonyl in which the alkoxy group contains 1 to 3 carbon atoms, and R'" is H or halo; $R_2$, $R_3$ and $R_4$ are each H; U is methylene; Q is a group of formula IIa in which V is methylene, E and E' are both ethylene and $R_5$ is H; and T is phenyl optionally substituted by hydroxy or one or more alkoxy groups.

In another group of preferred compounds of formula I, both A and B are —O—; g is 0; $G_1$—$G_2$—$G_3$ are —O—C(R')(R')—O— wherein R' is H, $R_2$, $R_3$ and $R_4$ are each H; U is methylene; Q is a group of formula IIa in which V is methylene, E and E' are both ethylene and $R_5$ is H; and T is phenyl optionally substituted by hydroxy or one or more alkoxy groups.

Compounds of formula I may exist as salts with pharmaceutically acceptable acids. The present invention includes all such salts. Examples of such salts include hydrochlorides, hydrobromides, sulphates, methanesulphonates, nitrates, maleates, acetates, citrates, fumarates, tartrates [eg (+)-tartrates, (−)-tartrates or mixtures thereof including racemic mixtures], succinates, benzoates and salts with amino acids such as glutamic acid.

It will be understood that any group mentioned herein which contains a chain of three or more atoms signifies a group in which the chain may be straight or branched. For example, an alkyl group may comprise propyl, which includes n-propyl and isopropyl, and butyl, which includes n-butyl, sec-butyl, isobutyl and tert-butyl. The term 'halo' as used herein signifies fluoro, chloro, bromo and iodo.

Compounds of formula I and intermediates in their preparation contain one or more chiral centres, and exist in different optically active forms. When compounds of formula I and intermediates in their preparation contain one chiral centre, the compounds exist in two enantiomeric forms and the present invention includes both enantiomers and mixtures of enantiomers. The enantiomers may be resolved by methods known to those skilled in the art, for example by formation of diastereoisomeric salts which may be separated, for example, by crystallisation; formation of diastereoisomeric derivatives or complexes which may be separated, for example, by crystallisation, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesised by asymmetric synthesis using optically active reagents, substrates, catalysts or solvents, or by converting one enantiomer into the other by asymmetric transformation.

When a compound of formula I contains more than one chiral centre it may exist in diastereoisomeric forms. The diastereoisomeric pairs may be separated by methods known to this skilled in the art, for example chromatography or crystallisation and the individual enantiomers within each pair may be separated as described above. The present invention includes each diastereoisomer of compounds of formula I and mixtures thereof.

Certain compounds of formula I and their salts may exist in more than one crystal form and the present invention includes each crystal form and mixtures thereof. Certain compounds of formula I and their salts may also exist in the form of solvates, for example hydrates, and the present invention includes each solvate and mixtures thereof.

Specific compounds of formula I are:
N-(9-Chloro-2,3-dihydrothieno[3,2-f][1,4]-benzodioxin-2-ylmethyl)1-[1-(2-methoxyphenyl)piperid-4-yl]methylamine;
N-(2,3-Dihydrothieno[3,2f]-1,4-benzodioxin-2-ylmethyl)-1-[1-(2-methoxyphenyl)piperid-4-yl]methylamine;
Ethyl 2,3-dihydro-2-(N-{[1-(2-methoxyphenyl)piperid-4-yl]methyl}aminomethyl)-7H-1,4-dioxino[2,3-e]indole-8-carboxylate;
N-(2,3-Dihydro-7H-1,4-dioxino[2,3-e]indol-2-ylmethyl)-1-[1-(2-methoxyphenyl)piperid-4-yl]methylamine;
N-(2,3-Dihydro-7H-1,4-dioxino[2,3-e]indazol-2-ylmethyl)-1-[1-(2-methoxyphenyl)-piperid-4-yl]methylamine;
N-(2,3-Dihydrofuro[3,2-f]-1,4-benzodioxin-2-ylmethyl)1-[1-(2-methoxyphenyl)piperid-4-yl]methylamine;
2-{4-[(2,3-Dihydrofuro[3,2-f]-1,4-benzodioxin-2-ylmethyl)aminomethyl]piperidino}phenol;
N-(7,8-Methylenedioxy-2,3-dihydro-1,4-benzodioxin-2-ylmethyl)-1-[1-(2-methoxyphenyl)piperid-4-yl]methylamine;
and pharmaceutically acceptable salts thereof in the form of individual enantiomers, racemates, or other mixtures of enantiomers.

Specific enantiomeric forms of compounds of formula I include:
(S)-N-(9-Chloro-2,3-dihydrothieno[3,2-f]-1,4-benzodioxin-2-ylmethyl)-1-[1-(2-methoxyphenyl)piperid-4-yl]methylamine;
(S)-N-(2,3-Dihydrothieno[3,2-f]-1,4-benzodioxin-2-ylmethyl)-1-[1-(2-methoxyphenyl)piperid-4-yl]methylamine;
Ethyl (S)-2,3-dihydro-2-(N-{[1-(2-methoxyphenyl)piperid-4-yl]methyl}aminomethyl)-7H-1,4-dioxino[2,3-e]indole-8-carboxylate;
(S)-N-(2,3-Dihydro-7H-1,4-dioxino[2,3-e]indol-2-ylmethyl)-1-[1-(2-methoxyphenyl)piperid-4-yl]methylamine;
(S)-N-(2,3-Dihydro-7H-1,4-dioxino[2,3-e]indazol-2-ylmethyl)-1-[1-(2-methoxyphenyl)piperid-4-yl]methylamine
(S)-N-(2,3-Dihydrofuro[3,2-f]-1,4-benzodioxin-2-ylmethyl)-1-[1-(2-methoxyphenyl)piperid-4-yl]methylamine
(S)-2-{4-[(2,3-Dihydrofuro[3,2-f]1,4-benzodioxin-2-ylmethyl)aminomethyl]piperidino}phenol;
(S)-N-(7,8-Methylenedioxy-2,3-dihydro-1,4-benzodioxin-2-ylmethyl)-1-[1-(2-methoxyphenyl)piperid-4-yl]methylamine
and pharmaceutically acceptable salts thereof.

The present invention also includes pharmaceutical compositions containing a therapeutically effective amount of a compound of formula I or a salt thereof together with a pharmaceutically acceptable diluent or carrier.

As used hereinafter, the term "active compound" denotes a compound of formula I or a salt thereof. In therapeutic use, the active compound may be administered orally, rectally, parenterally or topically, preferably orally. Thus the therapeutic compositions of the present invention may take the form of any of the known pharmaceutical compositions for oral, rectal, parenteral or topical administration. Pharmaceutically acceptable carriers suitable for use in such compositions are well known in the art of pharmacy. The compositions of the invention may contain 0.1–99% by weight of active compound. The compositions of the invention are generally prepared in unit dosage form. Preferably the unit dosage of active ingredient is 1–500 mg. The excipients used in the preparation of these compositions are the excipients known in the pharmacist's art.

Compositions for oral administration are the preferred compositions of the invention and these are the known pharmaceutical forms for such administration, for example tablets, capsules, syrups and aqueous or oil suspensions. The excipients used in the preparation of these compositions are the excipients known in the pharmacist's art. Tablets may be prepared by mixing the active compound with an inert diluent such as calcium phosphate in the presence of disintegrating agents, for example maize starch, and lubricating agents, for example magnesium stearate, and tableting the mixture by known methods. The tablets may be formulated in a manner known to those skilled in the art so as to give a sustained release of the compounds of the present invention. Such tablets may, if desired, be provided with enteric coatings by known methods, for example by the use of cellulose acetate phthalate. Similarly, capsules, for example hard or soft gelatin capsules, containing the active compound with or without added excipients, may be prepared by conventional means and, if desired, provided with enteric coatings in a known manner. The tablets and capsules may conveniently each contain 1 to 500 mg of the active compound. Other compositions for oral administration include, for example, aqueous suspensions containing the active compound in an aqueous medium in the presence of a non-toxic suspending agent such as sodium carboxymethylcellulose, and oily suspensions containing a compound of the present invention in a suitable vegetable oil, for example arachis oil.

The active compound may be formulated into granules with or without additional excipients. The granules may be ingested directly by the patient or they may be added to a suitable liquid carrier (for example water) before ingestion. The granules may contain disintegrants (for example a pharmaceutically acceptable effervescent couple formed from an acid and a carbonate or bicarbonate salt) to facilitate dispersion in the liquid medium.

Compositions of the invention suitable for rectal administration are the known pharmaceutical forms for such administration, for example, suppositories with cocoa butter or polyethylene glycol bases.

Pharmaceutical compositions may also be administered parenterally (for example subcutaneously, intramuscularly, intradermally and/or intravenously [such as by injection and/or infusion]) in the known pharmaceutical dosage forms for parenteral administration (for example sterile suspensions in aqueous and/or oily media and/or sterile solutions in suitable solvents, preferably isotonic with the blood of the intended patient). Parenteral dosage forms may be sterilised (for example by micro-filtration and/or using suitable sterilising agents [such as ethylene oxide]). Optionally one or more of the following pharmaceutically acceptable adjuvants suitable for parenteral administration may be added to parenteral dosage forms: local anaesthetics, preservatives, buffering agents and/or mixtures thereof. Parenteral dosage forms may be stored in suitable sterile sealed containers (for example ampoules and/or vials) until use. To enhance stability during storage the parenteral dosage form may be frozen after filling the container and fluid (for example water) may be removed under reduced pressure.

Pharmaceutical compositions may be administered nasally in known pharmaceutical forms for such administration (for example sprays, aerosols, nebulised solutions and/or powders). Metered dose systems known to those skilled in the art (for example aerosols and/or inhalers) may be used.

Pharmaceutical compositions may be administered to the buccal cavity (for example sub-lingually) in known pharmaceutical forms for such administration (for example slow dissolving tablets, chewing gums, troches, lozenges, pastilles, gels, pastes, mouthwashes, rinses and/or powders).

Compositions for topical administration may comprise a matrix in which the pharmacologically active compounds of the present invention are dispersed so that the compounds are held in contact with the skin in order to administer the compounds transdermally. A suitable transdermal composition may be prepared by mixing the pharmaceutically active compound with a topical vehicle, such as a mineral oil, petrolatum and/or a wax, for example paraffin wax or beeswax, together with a potential transdermal accelerant such as dimethyl sulphoxide or propylene glycol. Alternatively the active compounds may be dispersed in a pharmaceutically acceptable cream or ointment base. The amount of active compound contained in a topical formulation should be such that a therapeutically effective amount of the compound is delivered during the period of time for which the topical formulation is intended to be on the skin.

The compounds of the present invention may also be administered by continuous infusion either from an external source, for example by intravenous infusion or from a source of the compound placed within the body. Internal sources include implanted reservoirs containing the compound to be infused which is continuously released for example by osmosis and implants which may be (a) liquid such as a suspension or solution in a pharmaceutically acceptable oil of the compound to be infused for example in the form of a very sparingly water-soluble derivative such as a dodecanoate salt or ester or (b) solid in the form of an implanted support, for example of a synthetic resin or waxy material, for the compound to be infused. The support may be a single body containing all the compound or a series of several bodies each containing part of the compound to be delivered. The amount of active compound present in an internal source should be such that a therapeutically effective amount of the compound is delivered over a long period of time.

In some formulations it may be beneficial to use the compounds of the present invention in the form of particles of very small size, for example as obtained by fluid energy milling.

In the compositions of the present invention the active compound may, if desired, be associated with other compatible pharmacologically active ingredients.

The present invention also comprises a compound of formula I for use as a medicament.

The compounds of formula I or salts thereof or pharmaceutical compositions containing a therapeutically effective amount of a compound of formula I or a salt thereof may be used to treat depression, anxiety, psychoses (for example schizophrenia), tardive dyskinesia, Parkinson's disease, obesity, hypertension, Tourette's syndrome, sexual dysfunction, drug addiction, drug abuse, cognitive disorders, Alzheimer's disease, senile dementia, obsessive-compulsive behaviour, panic attacks, social phobias, eating disorders, anorexia, cardiovascular and cerebrovascular disorders, non-insulin dependent diabetes mellitus, hyperglycaemia, constipation, arrhythmia, disorders of the neuroendocrine system, stress, and spasticity in human beings. Preferably, the compounds of formula I are used to treat psychoses, for example schizophrenia. Whilst the precise amount of active compound administered in such treatment will depend on a number of factors, for example the age of the patient, the severity of the condition and the past medical history and always lies within the sound discretion of the administering physician, the amount of active compound administered per day is in the range 1 to 1000 mg preferably 5 to 500 mg given in single or divided doses at one or more times during the day.

A further aspect of the present invention provides the use of a compound of formula I in the manufacture of a medicament for treating depression, anxiety, psychoses (for example schizophrenia), tardive dyskinesia, Parkinson's disease, obesity, hypertension, Tourette's syndrome, sexual dysfunction, drug addiction, drug abuse, cognitive disorders, Alzheimer's disease, senile dementia, obsessive-compulsive behaviour, panic attacks, social phobias, eating disorders and anorexia, cardiovascular and cerebrovascular disorders, non-insulin dependent diabetes mellitus, hyperglycaemia, constipation, arrhythmia, disorders of the neuroendocrine system, stress, or spasticity in human beings. Preferably, there is provided a compound of formula I for use in the manufacture of a medicament for treating psychoses, for example schizophrenia.

The present invention also provides a method of treating depression, anxiety, psychoses (for example schizophrenia), tardive dyskinesia, Parkinson's disease, obesity, hypertension, Tourette's syndrome, sexual dysfunction, drug addiction, drug abuse, cognitive disorders, Alzheimer's disease, senile dementia, obsessive-compulsive behaviour, panic attacks, social phobias, eating disorders and anorexia, cardiovascular and cerebrovascular disorders, non-insulin dependent diabetes mellitus, hyperglycaemia, constipation, arrhythmia, disorders of the neuroendocrine system, stress, or spasticity in human beings which comprises the administration of a therapeutically effective amount of a compound of formula I to a patient in need thereof. Preferably, the method is a method of treating psychoses, for example schizophrenia.

Processes for the preparation of compounds of formula I will now be described. These processes form a further aspect of the present invention. The processes are preferably carried out at atmospheric pressure, at a temperature in the range minus 80° C. to 300° C. more preferably in the range 0–200° C., and most preferably in the range 20–150° C. The substituents are as defined for formula I above unless otherwise stated.

Compounds of formula I in which Q is a group of formula IIa in which $R_5$ is H, and V is $(CH_2)_n$ wherein n is 1, 2 or 3 may be prepared by reaction of a compound of formula III

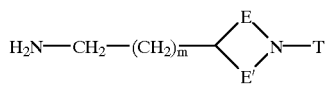

in which m is 0, 1 or 2, with a compound of formula IV

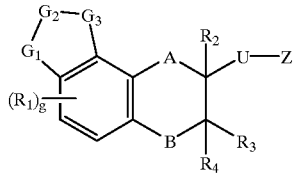

in which Z is a leaving group, for example toluene-4-sulphonyloxy, optionally in the presence of a suitable solvent, for example acetonitrile, optionally in the presence of a base, for example potassium carbonate, and optionally in the presence of a catalyst, for example potassium iodide.

Compounds of formula I in which U is methylene and Q is a group of formula IIa in which $R_5$ is H, and V is $(CH_2)_n$ wherein n is 1, 2 or 3, and R" and R'" are other than formyl may be prepared by reaction of a compound of formula V

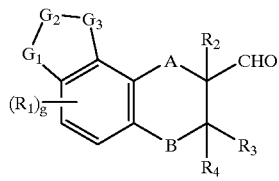

with a compound of formula III, followed by reduction of the intermediate imine with a suitable reducing agent, for example sodium borohydride.

Compounds of formula III and methods for their preparation are known (for example in WO95/07274).

Compounds of formula IV in which Z is toluene-4-sulphonyloxy may be prepared by reaction of a compound of formula VI

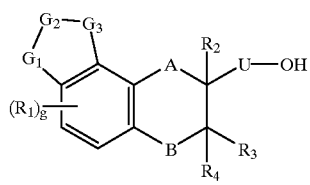

with toluene-4-sulphonyl chloride, optionally in the presence of a base, for example pyridine or 4-dimethylaminopyridine.

Compounds of formula VI in which A and B are both —O—, $R_2$, $R_3$ and $R_4$ are all H, and U is methylene may be prepared by reaction of a compound of formula VII

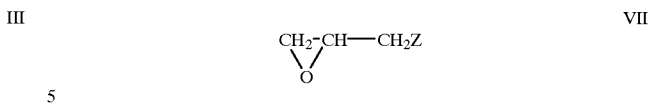

in which Z is a leaving group, for example chloro or toluene-4-sulphonyloxy, with a compound of formula VIII

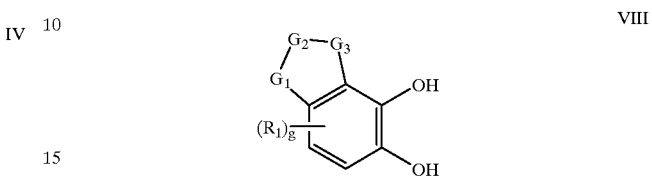

in a suitable solvent, for example water or dimethylformamide in the presence of a base, for example sodium hydroxide. When the appropriate enantiomerically pure form of a compound of formula VII, for example (R)-glycidyl 4-toluenesulphonate, is used, the single (S)-enantiomer of a compound of formula VI can be prepared.

Compounds of formula VI in which A and B are both —O—, U is methylene, and $R_2$, $R_3$ and $R_4$ are all H, may also be prepared by cyclisation of a compound of formula IX

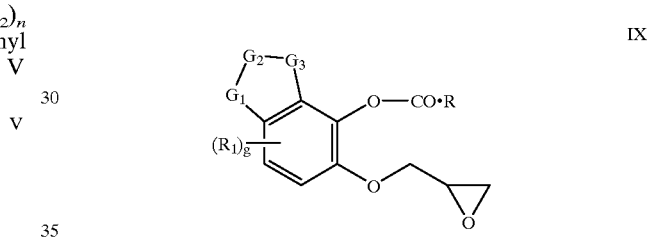

in which R is H or an alkyl group containing 1 to 4 carbon atoms, using a base, for example potassium carbonate.

Compounds of formula IX may be prepared by oxidation of compounds of formula X

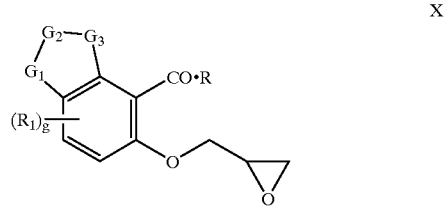

in which R is H or an alkyl group containing 1 to 4 carbon atoms, with a peroxyacid, for example 3-chloroperoxybenzoic acid.

Compounds of formula X may be prepared by alkylating compounds of formula XI

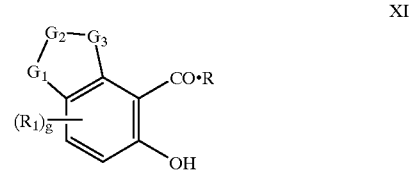

in which R is H or an alkyl group containing 1 to 4 carbon atoms, with compounds of formula VII, in which Z is a leaving group, for example chloro or toluene-4-sulphonyloxy, in a suitable solvent, for example dimethylformamide, in the presence of a base, for example potassium carbonate. When the appropriate enantiomerically pure form of a compound of formula VII, for example (R)-glycidyl 4-toluenesulphonate, is used, the single (S)-enantiomer of a compound of formula VI can be prepared.

Compounds of formula VI in which A and B are both —O—, U is methylene, $R_2$, $R_3$ and $R_4$ are all H, and the group —$G_1$—$G_2$—$G_3$— contains the group R" which is as stated below, may be prepared as follows:

- when R" is H or $CO_2Et$, the compound of formula VI may be prepared by cyclisation of the appropriate compound of formula IX in the presence of potassium carbonate;
- when R" is $CO_2H$, the compound of formula VI may be prepared by hydrolysis of the corresponding compound of formula VI in which R" is $CO_2Et$;
- when R" is H, the compound of formula VI may also be prepared by decarboxylation of the corresponding compound of formula VI in which R" is $CO_2H$;
- when R" is $CONH_2$, the compound of formula VI may be prepared by reaction of the corresponding compound of formula VI in which R" is $CO_2Et$, $CO_2H$, CO.Cl or $CO.O.CO_2Et$ with ammonia, in the presence, where appropriate, of an amide coupling agent such as carbonyl diimidazole;
- when R" is $CONMe_2$, the compound of formula VI may be prepared by reaction of the corresponding compound of formula VI in which R" is $CO_2Et$, $CO_2H$, CO.Cl or $CO.O.CO_2Et$ with dimethylamine, in the presence, where appropriate, of an amide coupling agent such as carbonyl diimidazole;
- when R" is CHO, the compound of formula VI may be prepared by reduction of the corresponding compound of formula VI in which R" is $CO_2Et$;
- when R" is COMe, the compound of formula VI may be prepared by reaction of the corresponding compound of formula VI in which R" is $CO_2H$ with methyl lithium; and
- when R" is CN, the compound of formula VI may be prepared by dehydration of the corresponding compound of formula VI in which R" is $CONH_2$.

Compounds of formula VI in which A and U are methylene, B is —O—, $R_2$ is H and R" and R'" are H or cyano, may be prepared by reduction of a compound of formula XII

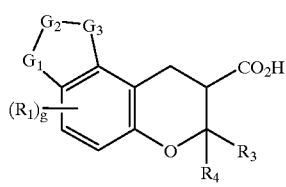

XII with a reducing agent, for example borane-dimethyl sulphide complex.

Compounds of formula XII may be prepared by reduction of a compound of formula XIII

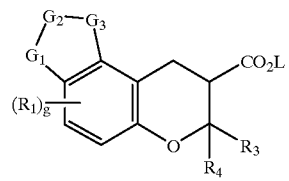

XIII in which L is H with a reducing agent, for example hydrogen in the presence of a palladium-on-carbon catalyst.

Compounds of formula XIII in which L is H may be prepared by acid or base-catalysed hydrolysis of a compound of formula XIII in which L is an alkyl group containing 1 to 6 carbon atoms.

Compounds of formula XIII in which L is an alkyl group may be prepared by reaction of a compound of formula XI in which R is H with a compound of formula XIV

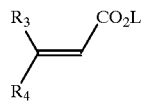

XIV in which L is an alkyl group containing 1 to 6 carbon atoms, in the presence of a base, for example 1,4-diazabicyclo[2.2.2]octane (DABCO).

Compounds of formula V may be prepared by oxidation of a compound of formula VI in which U is methylene with a suitable oxidising agent, for example pyridinium chlorochromate or by reduction of a compound of formula XV

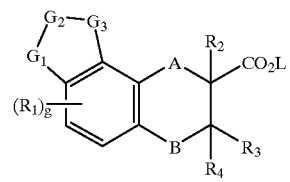

XV with a suitable reducing agent, for example sodium bis(2-methoxyethoxy)aluminium hydride in a solvent, for example toluene.

Compounds of formula XV in which A and B are both —O— may be prepared by reaction of a compound of formula XVI

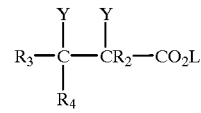

XVI in which Y is a leaving group, for example bromo, and L is an alkyl group containing 1 to 6 carbon atoms with a compound of formula VIII, in the presence of a base, for example potassium carbonate.

Compounds of formula XV in which A is methylene, B is —O—, $R_2$ is H and L is an alkyl group containing 1 to 6 carbon atoms may be prepared by reduction of a compound of formula XIII in which L is an alkyl group containing 1 to 6 carbon atoms, with a suitable reducing agent, for example hydrogen in the presence of a palladium-on-carbon catalyst.

Compounds of formula I in which Q is a group of formula IIb may be prepared by reaction of a compound of formula IV in which Z is a leaving group, for example toluene-4-sulphonyloxy, with a compound of formula XVII

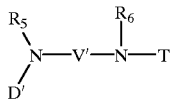

XVII in which D' is H, optionally in the presence of a base, for example potassium carbonate, and optionally in a solvent, for example acetonitrile.

Compounds of formula XVII in which D' is H may be prepared by deprotection of a compound of formula XVII in which D' is a protecting group, for example tert-butoxycarbonyl, for example by hydrolysis in the presence of an acid, for example trifluoroacetic acid.

Compounds of formula XVII in which D' is a protecting group may be prepared by reaction of a compound of formula XVIII

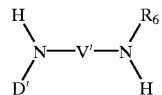

XVIII in which D' is a protecting group, for example tert-butoxycarbonyl, with a haloaromatic compound, for example a 2-halopyridine such as 2-chloropyridine, optionally in the presence of a base, for example triethylamine, in a suitable solvent such as dichloromethane.

Compounds of formula I in which Q is a group of formula IIc in which V is $(CH_2)_n$ wherein n is 1, 2, or 3 may be prepared by reaction of a compound of formula XIX

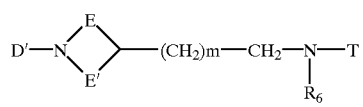

XIX in which D' is H and m is 0, 1 or 2, with a compound of formula IV in which Z is a leaving group, for example toluene-4-sulphonyloxy, optionally in the presence of a base, for example potassium carbonate, and optionally in a solvent, for example acetonitrile.

Compounds of formula XIX in which D' is H may be prepared by deprotection of a compound of formula XIX in which D' is a protecting group, for example tert-butoxycarbonyl, for example by hydrolysis in the presence of an acid, for example trifluoroacetic acid.

Compounds of formula XIX in which D' is a protecting group may be prepared by reaction of a compound of formula XX

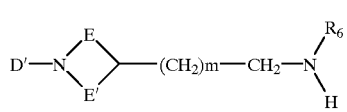

XX in which D' is a protecting group, for example tert-butoxycarbonyl, and m is 0, 1 or 2, with a haloaromatic compound, for example a 2-halopyridine such as 2-chloropyridine, optionally in the presence of a base, for example triethylamine, in a suitable solvent such as dichloromethane.

Compounds of formula IV in which $G_1$—$G_2$—$G_3$ are —NH—CH=CH— are known (J.Med.Chem.,1992,35, pg 3058).

Compounds of formula IV in which $G_1$—$G_2$—$G_3$ are other than —NH—CH=CH— may be prepared by methods analogous to that described above.

Compounds of formula I in which $R_5$ is an alkyl group and R'' and R''' are other than formyl may be prepared by alkylation of a compound of formula I in which $R_5$ is H with for example formaldehyde and formic acid, or an aldehyde and a reducing agent such as sodium cyanoborohydride.

Compounds of formula XI in which R is H may be prepared by reaction of a compound of formula XXI

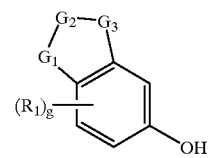

XXI with an N-arylformimidate ester of formula XXII

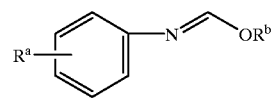

XXII in which $R^a$ is H, an alkyl group containing 1 to 3 carbon atoms, an alkoxy group containing 1 to 3 carbon atoms, or halo, and $R^b$ is an alkyl group containing 1 to 3 carbon atoms, for example ethyl N-(4-methoxyphenyl)formimidate, followed by hydrolysis of the intermediate imine in the presence of an acid.

Compounds of formula XI in which R=H and $G_1$—$G_2$—$G_3$ represents —O—C(R')$_2$—O— may be prepared by reaction of a compound of formula XXIII

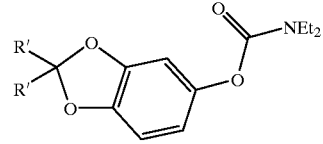

XXIII with a lithiating agent, for example sec-butyllithium, followed by a formylating agent, for example N,N-dimethylformamide, followed by hydrolytic work-up.

Compounds of formula XXIII may be prepared by reaction of compounds of formula XXI with diethylcarbamoyl chloride in the presence of a base, for example sodium hydride.

Compounds of formula I in which the group T bears a hydroxy substituent may be prepared by dealkylation of a corresponding alkoxy substituted compound, by reaction with a dealkylating agent, for example pyridine hydrochloride.

Compounds of formula I in which $G_1$—$G_2$—$G_3$ represents —S—CH=CH— may be prepared by dechlorination of a corresponding compound in which $G_1$—$G_2$—$G_3$ represents —S—CH=CCl— by, for example, reaction with hydroiodic acid.

The ability of compounds of formula I to interact with 5-hydroxytryptamine (5-HT) receptors has been demonstrated by the following test which determines the ability of the compounds to inhibit tritiated ligand binding to 5-HT receptors in vitro and in particular to 5-HT$_{1A}$ receptors.

Hippocampal tissue from the brains of male Charles River CD rats weighing between 150–250 g were homogenised in ice-cold 50 mM Tris-HCl buffer (pH 7.7) when measured at 25° C., 1:40 w/v) and centrifuged at 30,000 g at 4° C. for 10 minutes. The pellet was rehomogenised in the same buffer, incubated at 37° C. for 10 minutes and centrifuged at 30,000 g at 4° C. for 10 minutes. The final pellet was resuspended in 50 mM Tris-HCl buffer (pH 7.7) containing 4 mM $CaCl_2$, 0.1% L-ascorbic acid and 10 μM pargyline hydrochloride (equivalent to 6.25 mg wet weight of tissue/ml) and used immediately in the binding assay. Aliquots (400 μl; equivalent to 2.5 mg wet weight of tissue/tube) of this suspension were added to tubes containing the ligand (50 μl; 2 nM) and distilled water (50 μl; total binding) or 5-HT (50 μl; 10 μM; non-specific binding) or test compound (50 μl; at a single concentration of $10^{-6}$ M or at 10 concentrations ranging from $10^{-}$–$10^{-3}$ M). The ligand was [$^3$H]8-hydroxy-2-(dipropylamino)tetralin ([$^3$H]8—OH-DPAT) and the mixture was incubated at 25° C. for 30 minutes before the incubation was terminated by rapid filtration.

The filters were washed with ice-cold Tris-HCl buffer and dried. The filters were punched out into vials, scintillation fluid added and radioactivity determined by liquid scintillation counting. The percentage displacement of specific binding of the tritiated ligand was calculated for the single concentration ($10^{-6}$ M) of test compound. Displacement curves were then produced for those compounds which displaced ≧50% of specific binding of the tritiated ligand at $10^{-6}$ M using a range of concentrations of the compound. The concentration which gave 50% inhibition of specific binding (IC$_{50}$) was obtained from the curve. The inhibition coefficient Ki was then calculated using the formula $$K_i = \frac{IC50}{1+([ligand]/K_D)}$$

in which [ligand] is the concentration of the tritiated ligand used and $K_D$ is the equilibrium dissociation constant for the ligand.

The ability of compounds of formula I to interact with dopamine receptors has been demonstrated by the following test which determines the ability of the compounds to inhibit tritiated ligand binding to dopamine receptors in vitro and in particular to the $D_2$-like dopamine receptors.

Striatal tissue from the brains of male Charles River CD rats weighing between 140–250 g were homogenised in ice-cold 50 mM Tris-HCl buffer (pH 7.7 when measured at 25° C.) and centrifuged at 40,000 g for 10 minutes. The pellet was resuspended in Tris salts buffer (50 mM Tris-HCl buffer containing 120 mM NaCl, 5 mM KCl, 2 mM $CaCl_2$ and 1 mM $MgCl_2$ with the addition of 6 mM ascorbic acid; pH 7.7 when measured at 25° C.), and again centrifuged at 40,000 g for 10 minutes. The final pellet was stored at –80° C. Before each test the pellet was resuspended in Tris salts buffer (equivalent to 2 mg wet weight of tissue/ml). Aliquots (720 μl; equivalent to 1.44 mg wet weight of tissue/tube) of this suspension were then added to tubes containing the ligand (40 μl; 1 nM) and Tris salts buffer (40 μl; total binding) or spiroperidol (40 μl; 10 nM; non-specific binding) or test compound (40 μl; at a single concentration of $10^{-6}$ M or at 6 concentrations ranging from $10^{-11}$–$10^{-4}$M). The ligand was tritiated (S)-sulpiride and the mixture was incubated at 4° C. for 40 minutes before the incubation was terminated by rapid filtration.

The filters were washed with ice-cold Tris-HCl buffer and dried. The filters were punched out in to vials, scintillation fluid added and were left for about 20 hours before being counted by scintillation spectrophotometry. The percentage displacement of specific binding of the tritiated ligand was calculated for the single concentration ($10^{-6}$M) of test compound. Displacement curves were then produced over a range of concentrations for those compounds which displaced ≧50% of specific binding of the tritiated ligand at $10^{-6}$M. The concentration which gave a 50% inhibition of specific binding (IC50) was obtained from the curve. The inhibition coefficient Ki was then calculated using the formula $$K_i = \frac{IC50}{1+([ligand]/K_D)}$$

in which [ligand] is the concentration of the tritiated ligand used and $K_D$ is the equilibrium dissociation constant for the ligand.

The $K_i$ values obtained in the above tests for 5-HT$_{1A}$ and $D_2$-like binding for each of the final products of the Examples hereinafter are given in Table I below.

TABLE 1

| Example | Ki (nM) value for | |
| --- | --- | --- |
| Number | 5-HT$_{1A}$ | $D_2$-like |
| 1 | 36 | 76.9 |
| 2 | 9.7 | 40.4 |
| 3 | 99% | 106 |
| 4 | 99% | 8.96 |
| 5 | 1.2 | 7.1 |
| 6 | 1.7 | 22.1 |
| 7 | 3.6 | 11.7 |
| 8 | 1.1 | 6 |

The % figures in Table 1 are for % displacement at $10^{-6}$M.

Advantageous compounds of the present invention have a Ki of less than 100 nM for 5-HT$_{1A}$ or a binding affinity for 5-HT$_{1A}$ of greater than 90% at $10^{-6}$M and a Ki of less than 100 nM for $D_2$-like receptors or a binding affinity for $D_2$-like receptors of greater than 90% at $10^{-6}$M.

The invention is illustrated by the following Examples which are given by way of example only. The final product of each Example was characterised by one or more of the following procedures: gas-liquid chromatography; high performance liquid chromatography; elemental analysis, nuclear magnetic resonance spectroscopy, infrared spectroscopy and spectroscopy.

EXAMPLE 1

A stirred solution of ethyl 3-chloro-5-methoxybenzo[b]thiophene-2-carboxylate (20.0 g) in dichloromethane (80 ml) at –20° C. under an atmosphere of nitrogen was treated with boron tribromide (1M solution in dichloromethane; 90 ml) and the solution allowed to warm up to room temperature slowly. After 2 hours the mixture was carefully poured into ethanol (400 ml) and left to stand for 10 minutes. The solvent was evaporated under reduced pressure and the residue dissolved in ethyl acetate (500 ml). The resulting solution was washed with water (300 ml), dried over sodium sulphate and the solvent evaporated under reduced pressure to give ethyl 3-chloro-5-hydroxybenzo[b]thiophene-2-carboxylate (18.68 g) as an off-white solid; m.p. 160–161° C.

A round bottomed flask containing a mixture of the product from the previous reaction (6.04 g) and ethyl N-(4-methoxyphenyl)formimidate (4.50 g) was submerged rapidly in an oil bath pre-heated to 160° C., and the mixture stirred at 160–80° C. for 4 hours, the ethanol produced in the reaction being removed by distillation. More of the formimidate (0.80 g) was then added and the mixture heated at 180–90° C. for a further 1 hour. The cooled mixture was then treated with boiling methanol (100 ml) and the resulting light brown solid collected by filtration, washed with methanol (100 ml) and dried to give ethyl 3-chloro-5-hydroxy-4-[N-(4-methoxyphenyl)iminomethyl]benzo[b]thiophene-2-carboxylate (4.03 g); m.p. 162–163° C.

A stirred mixture of the product from the previous reaction (3.82 g) and hydrochloric acid (4M; 130 ml) was heated at 50–60° C. for 4 hours and then left to stand at room temperature overnight. The mixture was then heated at 60–70° C. for 3 hours. The cooled mixture was poured into water (350 ml) and extracted with ethyl acetate (2×250 ml). The combined organic extracts were washed with water (200 ml), dried over sodium sulphate and evaporated under reduced pressure to give ethyl 3-chloro-4-formyl-5-hydroxybenzo[b]thiophene-2-carboxylate (2.80 g) as a pale-green solid; m.p. 128–130° C.

Potassium carbonate (2.62 g) was added to a stirred solution of ethyl 3-chloro-4-formyl-5-hydroxybenzo[b]thiophene-2-carboxylate (4.90 g, prepared as described above) in dry dimethylformamide (50 ml) and then a solution of (R)-glycidyl tosylate (4.12 g) in dry dimethyl formamide (50 ml) was added slowly. The mixture was then stirred at 60° C. for 3 hours, cooled and poured into water (1200 ml). The resulting pale-green solid was collected by filtration, washed with water (200 ml) and dried to give ethyl (R)-3-chloro-5-(2,3-epoxypropoxy)-4-formylbenzo[b]thiophene-2-carboxylate (5.15 g).

A stirred solution of the product from the previous reaction (1.0 g) in dichloromethane (20 ml) was treated with 3-chloroperoxybenzoic acid (85%; 0.75 g) and the mixture cooled to 0° C. A solution of trifluoroacetic acid (0.335 g) in dichloromethane (5 ml) was then added and the solution stirred at 0° C. for 5 minutes and then at room temperature for 1 hour. The mixture was poured into saturated aqueous sodium bisulphite solution (100 ml) and extracted with dichloromethane (2×100 ml). The combined organic extracts were washed with saturated aqueous sodium bicarbonate solution (2×150 ml), dried over sodium sulphate and evaporated under reduced pressure to give a brown oil. Purification by flash chromatography on silica using a 1:1 mixture of petroleum ether (b.p. 60–80° C.) and ethyl acetate as eluant gave ethyl (R)-3-chloro-5-(2,3-epoxypropoxy)-4-formyloxybenzo[b]thiophene-2-carboxylate (0.52 g) as a pale-yellow solid.

Saturated aqueous potassium carbonate solution (20 ml) was added to a stirred solution of ethyl (R)-3-chloro-5-(2,3-epoxypropoxy)-4-formyloxy-benzo[b]thiophene-2-carboxylate (1.85 g, prepared as described above) in tetrahydrofuran (20 ml) and the mixture stirred for 24 hours at room temperature. The reaction mixture was poured into water (200 ml) and extracted with ethyl acetate (2×100 ml). The combined extracts were dried over sodium sulphate and evaporated under reduced pressure to give a yellow solid. Purification by flash chromatography on silica using a 1:1 mixture of petroleum ether (b.p. 60–80° C.) and ethyl acetate as eluant gave ethyl (S)-9-chloro-2,3-dihydro-2-(hydroxymethyl)thieno[3,2-f]-1,4-benzodioxin-8-carboxylate (1.44 g) as a pale-yellow solid; m.p. 165–166° C.

A stirred solution of the product from the previous reaction (1.30 g) in methanol (20 ml) was treated with a solution of lithium hydroxide monohydrate (0.17 g) in water (10 ml) and the mixture heated at 60° C. for 1 hour. The solution was evaporated under reduced pressure to remove methanol and then diluted with water (50 ml). The aqueous solution was acidified with hydrochloric acid (2 M) and the resulting suspension collected by filtration, washed with water and dried to give (S)-9-chloro-2,3-dihydro-2-(hydroxymethyl)thieno[3,2-f]-1,4-benzodioxin-8-carboxylic acid (1.15 g) as an off-white solid, m.p. 236–7° C.

A round bottomed flask containing a mixture of the product from the previous reaction (0.80 g), copper powder (0.17 g) and quinoline (10 ml) was rapidly submerged in an oil bath pre-heated to 190° C., and the mixture heated with stirring at this temperature for 30 minutes. The mixture was cooled to room temperature and poured into hydrochloric acid (2M; 300 ml). The mixture was extracted with ethyl acetate (2×150 ml) and the combined extracts washed with hydrochloric acid (2M; 150 ml), water (150 ml), then dried over sodium sulphate and evaporated under reduced pressure to give a dark brown oil (0.781 g). Purification by flash chromatography on silica using a 3:10 mixture of ethyl acetate and petroleum ether (b.p. 60–80° C.) as eluant gave (S)-9-chloro-2,3-dihydro-2-(hydroxymethyl)thieno[3,2-f]-1,4-benzodioxin (0.70 g) as a white solid, m.p. 92–3° C.

4-Dimethylaminopyridine (0.26 g) then 4-toluenesulphonyl chloride (0.40 g) were added to a stirred solution of (S)-9-chloro-2,3-dihydro-2-(hydroxymethyl)thieno[3,2f]-[1,4]-benzodioxin (0.49 g) in dichloromethane (20 ml), and the mixture then stirred at ambient temperature for 24 hours. The resulting solution was poured into water (100 ml) and extracted with dichloromethane (150 ml). The resulting organic solution was then washed successively with saturated copper sulphate solution (2×100 ml) and water (100 ml). The solution was dried over sodium sulphate and the solvent evaporated under reduced pressure to give (S)-9-chloro-2,3-dihydrothieno[3,2-f]-1,4-benzodioxin-2-ylmethyl 4-toluenesulphonate (0.7 g) as a white solid m.p. 169–70° C.

A stirred mixture of the product from the previous reaction (0.63 g), potassium carbonate (3.0 g) and 1-[1-(2-methoxyphenyl)piperid-4-yl]methylamine (0.40 g) in dry acetonitrile (25 ml) was heated under reflux for 24 hours. The mixture was cooled, filtered and then evaporated under reduced pressure. The residue was dissolved in dichloromethane (150 ml), washed with water (100 ml), dried over sodium sulphate and the solvent evaporated under reduced pressure to give a pale-yellow oil (1.08 g). Purification by flash column chromatography on silica eluting with a 20:1 mixture of dichloromethane and methanol gave a colourless oil (0.47 g). The oil was dissolved in warm ethanol (2 ml) and a solution of fumaric acid (122 mg) in warm ethanol (2 ml) then added. The resulting white solid was collected by filtration and dried to give (S)-N-(9-chloro-2,3-dihydrothieno[3,2-f]-1,4-benzodioxin-2-ylmethyl)-1-[1-(2-methoxyphenyl)piperid-4-yl]methylamine 0.5 fumarate (0.40 g) m.p. 171–172° C., $[\alpha]_D$ −30.4° (c=0.237, MeOH).

EXAMPLE 2

A stirred mixture of (S)-(−)-N-(9-chloro-2,3-dihydrothieno[3,2-f][1,4]-benzodioxin-2-ylmethyl)-1-[1-(2-methoxyphenyl)piperid-4-yl]methylamine, prepared by the method described above (2.64 g) and hydroiodic acid (57%; 100 ml) was heated at 60–70° C. for 6 hours and then allowed to stand at room temperature for 18 hours. The mixture was poured into aqueous ammonia (250 ml) and extracted with ethyl acetate (3×150 ml). The combined extracts were then washed with brine (200 ml), dried over sodium sulphate and the solvent evaporated under reduced pressure to leave a brown oil (2.72 g). Purification by flash column chromatography on silica eluting with a 95:5 mixture of dichloromethane and methanol, followed by repeat chromatography eluting with a 98:2 mixture of dichloromethane and methanol, gave a colourless oil (0.65 g). Fumaric acid (0.178 g) in ethanol (10 ml) was then added to a solution of the oil in ethanol (5 ml) and the solvent then removed under reduced pressure to give (S)-N-(2,3-dihydrothieno[3,2-f]1,4-benzodioxin-2-ylmethyl)1-[1-(2-methoxyphenyl)piperid-4-yl]methylamine monofumarate (0.78 g) as an off-white solid; m.p. 180–182° C., $[\alpha]_D$ –28.1° (c=0.498, DMSO)

EXAMPLE 3

Potassium carbonate (0.89 g) was added under nitrogen to a stirred solution of ethyl 4-formyl-5-hydroxyindole-2-carboxylate (1.50 g) in dry dimethylformamide (40 ml). A solution of (R)-glycidyl 4-toluenesulphonate (1.47 g) in dry dimethylformamide (30 ml) was then added and the mixture stirred at ambient temperature for 10 minutes, then at 60° C. for 3 hours. The mixture was poured into water (400 ml) and extracted with ethyl acetate (3×200 ml). The combined extracts were washed with brine (6×200 ml), dried over magnesium sulphate and the solvent evaporated under reduced pressure. The brown solid residue was purified by flash column chromatography on silica eluting with a 1:1 mixture of petroleum ether (b.p. 40–60° C.) and ethyl acetate to give ethyl (R)-5-(2,3-epoxypropoxy)-4-formylindole-2-carboxylate (1.07 g) as an off-white solid; m.p. 152–154° C.

A stirred solution of ethyl (R)-5-(2,3-epoxypropoxy)-4-formylindole-2-carboxylate (1.95 g; prepared by the method described above) in dichloromethane (40 ml) was cooled to 0° C. 3-Chloroperoxybenzoic acid (85%; 1.75 g) was then added in one portion followed by a solution of trifluoroacetic acid (0.77 g) in dichloromethane (10 ml), in portions. The mixture was stirred at 0° C. for 10 minutes and then at ambient temperature for 1 hour. The reaction mixture was diluted with dichloromethane (300 ml), washed successively with saturated aqueous sodium bisulphite solution (100 ml), saturated aqueous sodium bicarbonate solution (3×150 ml), dried over sodium sulphate and the solvent evaporated. The solid residue was purified by flash chromatography on silica eluting with a 1:1 mixture of petroleum ether (b.p. 40–60° C.) and ethyl acetate to give ethyl (R)-5-(2,3-epoxypropoxy)-4-formyloxyindole-2-carboxylate (1.55 g) as a pale yellow crystalline solid; m.p. 123–125° C.

Saturated aqueous potassium carbonate solution (200 ml) was added to a stirred solution of ethyl (R)-5-(2,3-epoxypropoxy)-4-formyloxyindole-2-carboxylate (22.0 g; prepared in a similar manner to that described above) in tetrahydrofuran (250 ml) and the mixture was stirred at room temperature for 72 hours. The mixture was poured into water (1000 ml) and extracted with ethyl acetate (4×400 ml). The combined extracts were dried over sodium sulphate and the solvent evaporated under reduced pressure to give ethyl (S)-2,3-dihydro-2-(hydroxymethyl)-7H-1,4-dioxino[2,3-e] indole-8-carboxylate (17.65 g) as a pale purple solid; m.p. 152–153° C.

4-Toluenesulphonyl chloride (2.23 g) was added in one portion to a stirred solution of ethyl (S)-2,3-dihydro-2-(hydroxymethyl)-7H-1,4-dioxino]2,3-e]indole-8-carboxylate (2.65 g) in dry dichloromethane (120 ml) at 0° C. 4-Dimethylaminopyridine (1.52 g) was then added and the cooling bath removed. The resulting solution was stirred at ambient temperature for 72 hours, then diluted with dichloromethane (150 ml) and washed successively with water (80 ml), saturated aqueous copper sulphate solution (2×100 ml), and then dried over sodium sulphate. Evaporation of the solvent under reduced pressure gave a purple foam which was purified by flash column chromatography on silica eluting with a 1:1 mixture of petroleum ether (b.p. 40–60° C.) and ethyl acetate, to give ethyl (S)-2,3-dihydro-2-[(4-toluenesulphonyloxy)methyl]-7H-1,4-dioxino[2,3-e] indole-8-carboxylate (3.71 g) as a colourless oil which solidified on standing.

A mixture of the product from the previous reaction (1.0 g), potassium carbonate (3.0 g) and 1-[1-(2-methoxyphenyl) piperid-4-yl]methylamine (0.80 g) in dry acetonitrile (50 ml) was heated under reflux with stirring for 24 hours. The cooled mixture was filtered and then evaporated under reduced pressure to give a yellow oil. The crude material was dissolved in dichloromethane (200 ml), washed with water (150 ml), dried over sodium sulphate and evaporated under reduced pressure to give a yellow oil (1.65 g). Purification by flash column chromatography on silica eluting with a 20:1 mixture of dichloromethane and methanol gave ethyl (S)-2,3-dihydro-2-(N-{[1-(2-methoxyphenyl) piperid-4-yl]methyl}aminomethyl)-7H-1,4-dioxino[2,3-e] indole-8-carboxylate 0.05 dichloromethane solvate (0.34 g) as an off-white solid m.p. 105–107° C., $[\alpha]_D$ –24° (c=0.409, MeOH).

EXAMPLE 4

A solution of lithium hydroxide monohydrate (0.94 g) in water (25 ml) was added to a stirred solution of the product from the previous reaction (2.95 g) in methanol (50 ml) under nitrogen and the resulting solution stirred at 60° C. for 1 hour. The methanol was then removed by evaporation and water (80 ml) added. Hydrochloric acid (2M) was then added until the mixture was pH 2, and the resulting precipitate collected by filtration, washed with water and dried to give (S)-2,3-dihydro-2-(hydroxymethyl)-7H-1,4-dioxino[2,3-e]indole-8-carboxylic acid (2.61 g) as a solid; m.p. 216–217° C.

A flask containing the product from the previous reaction (2.60 g) was plunged into a pre-heated isomantle at 250° C. under nitrogen and the material heated at 250–60° C. for 30 minutes. The residue was cooled to ambient temperature, pre-absorbed from a methanol solution onto silica and purified by flash column chromatograhy on silica eluting with 1:1 mixture of petroleum ether (b.p. 40–60° C.) and ethyl acetate to give (S)-2,3-dihydro-7H-1,4-dioxino-[2,3-e]indol-2-ylmethanol (0.69 g) as a colourless syrup.

A solution of (S)-2,3-dihydro-7H-1,4-dioxino[2,3-e] indol-2-ylmethanol (0.75 g; prepared by the method described above) in dichloromethane (50 ml) was stirred with cooling in an ice bath. 4-(Dimethylamino)pyridine (0.59 g) and 4-toluenesulphonyl chloride (0.84 g) were then added and the solution stirred at ambient temperature overnight. The mixture was diluted with dichloromethane (200 ml), washed sucessively with water (50 ml), saturated aqueous copper(II) sulphate solution (2×50 ml) and water (50 ml), then dried over sodium sulphate and the solvent evaporated to give (S)-2,3-dihydro-7H-1,4-dioxino[2,3-e]indol-2-ylmethyl 4-toluenesulphonate (1.04 g) as a pale brown oil which solidified on standing.

A mixture of (S)-2,3-dihydro-7H-1,4-dioxino[2,3-e] indol-2-ylmethyl 4-toluenesulphonate (2.76 g; prepared in a similar manner to that described above), potassium carbonate (8.0 g) and 1-[1-(2-methoxyphenyl)piperid-4-yl]methylamine (1.86 g) in dry acetonitrile (60 ml) was heated under reflux with stirring for 24 hours. The cooled mixture was filtered, the solid washed with dichloromethane (100 ml) and the filtrate then evaporated under reduced pressure. The residue was dissolved in dichloromethane (250 ml) and the resulting solution washed with water (100 ml), dried over sodium sulphate and evaporated under reduced pressure to give a fawn solid (4.51 g). Purification by flash column chromatography on silica eluting with a 20:1 mixture of dichloromethane and methanol gave (S)-N-(2,3-dihydro-7H-1,4-dioxino[2,3-e]indol-2-ylmethyl)-1-[1-(2-methoxyphenyl)piperid-4-yl]methylamine 0.1 hydrate (1.34 g) as an off-white crystalline solid m.p. 162–163° C., $[\alpha]_D$ −18.50° (c=0.541, $CH_2Cl_2$).

EXAMPLE 5

A round bottomed flask containing a mixture of 5-hydroxy-1H-indazole (28.5 g) and ethyl N-phenylformimidate (35 g) was submerged rapidly in an oil bath pre-heated to 175° C. and the mixture stirred at 160–180° C. for 30 minutes, the ethanol produced in the reaction being removed by distillation. The cooled mixture was then treated with boiling methanol (500 ml) and the resultant brown solid collected by filtration, washed with methanol (100 ml) and dried to give 5-hydroxy-4-(N-phenyliminomethyl)-1H-indazole (32 g) as a yellow solid. The solid was dissolved in hydrochloric acid (5 M; 500 ml) and heated at 50–60° C. with stirring for 2 hours. The mixture was diluted with water (500 ml) and extracted with ethyl acetate (2×500 ml). The combined extracts were washed with water (500 ml), dried over magnesium sulphate and the solvent evaporated under reduced pressure to give 5-hydroxy-1H-indazole-4-carboxaldehyde (15.48 g) as a yellow solid.

A mixture of potassium carbonate (11 g), the product from the previous reaction (12.5 g) and (R)-glycidyl tosylate (20 g) in dimethylformamide (250 ml) was stirred and heated at 50° C. under an atmosphere of nitrogen for 3 hours. The mixture was poured into water (1000 ml) and extracted with ethyl acetate (3×300 ml). The combined extracts were washed with water (2×300 ml), dried over magnesium sulphate and the solvent evaporated under reduced pressure. The yellow solid residue was then purified by flash column chromatography on silica eluting with a 1:1 mixture of petroleum ether (b.p. 60–80° C.) and ethyl acetate to give (R)-5-(2,3-epoxypropoxy)-1H-indazole-4-carboxaldehyde (2.58 g) as a pale yellow solid.

A solution of the product from the previous reaction (2.58 g) and 3-chloroperoxybenzoic acid (56–87%; 12.2 g) in dichloromethane (300 ml) was stirred at 0° C. for 2 hours. The mixture was then evaporated to dryness and the residue dissolved in sodium hydroxide solution (2.5 M; 200 ml). The navy blue solution was then heated on the steam bath for 1 hour with a resultant colour change to deep orange. The cooled reaction mixture was diluted with water (200 ml) and extracted with ethyl acetate (3×250 ml). The combined extracts were washed with brine (250 ml), dried over magnesium sulphate and the solvent evaporated under reduced pressure to afford (S)-2-hydroxymethyl-7H-1,4-dioxino[2,3-e]indazole (0.97 g) as a cream solid.

A solution of 4-toluenesulphonyl chloride (2 g) in dichloromethane (100 ml) was added dropwise to a stirred solution the product from the previous reaction (0.95 g) and 4-dimethylaminopyridine (1.2 g) in dichloromethane (100 ml) at 0–5° C. The mixture was allowed to warm to room temperature and stirred for 18 hours. The solution was diluted with dichloromethane (30 ml) and washed successively with water (100 ml), dilute aqueous sodium hydrogen carbonate solution (5M; 2×100 ml), brine (2×100 ml) and then dried over magnesium sulphate. Evaporation of the solvent under reduced pressure gave a white solid residue which was then purified by flash column chromatography on silica using a 99:1 mixture of dichloromethane and ethyl acetate as eluant. The (S)-7-(4-toluenesulphonyl)-2,3-dihydro-7H-1,4-dioxino[2,3-e]indazol-2-ylmethyl 4-toluenesulphonate produced which was dissolved in a mixture of 48% hydrobromic acid (2 ml) and phenol (0.4 g) and heated under reflux for 30 minutes. The cooled mixture was basified with sodium hydroxide (5M) and extracted with dichloromethane (3×25 ml). The combined extracts were washed with water (25 ml), dried over magnesium sulphate and the solvent removed under reduced pressure. The residue was purified by flash column chromatography on silica eluting with a 10:1 mixture of petroleum ether (b.p. 60–80° C.) and ethyl acetate to give (S)-2,3-dihydro-7H-1,4-dioxino[2,3-e]indazol-2-ylmethyl 4-toluenesulphonate (0.53 g) as a white solid.

A mixture of the product from the previous reaction (0.25 g), potassium carbonate (2 g) and 1-[1-(2-methoxyphenyl)piperid-4-yl]methylamine (0.3 g) in a mixture of dimethylformamide (5 ml) and toluene (10 ml) was heated at reflux temperature for 8 hours. The cooled mixture was poured into water (100 ml) and extracted with ethyl ether (2×100 ml). The combined extracts were then dried over magnesium sulphate and the solvent removed under reduced pressure to yield a yellow oil. Purification by flash column chromatography on silica eluting with a 20:1 mixture of dichloromethane and methanol afforded (S)-N-(2,3-dihydro-7H-1,4 -dioxino[2,3-e]indazol-2-ylmethyl)-1-[1-(2-methoxyphenyl)piperid-4-yl]methylamine (0.04 g) as a gummy solid.

EXAMPLE 6

Potassium carbonate (2.85 g) and a solution of (R)-glycidyl 4-toluensulphonate (4.50 g) in dry dimethylformamide (10 ml) were added to a stirred solution of 5-hydroxybenzo[b]furan-4-carboxaldehyde (3.04 g) in dry dimethylformamide (30 ml). The mixture was heated at 60° C. for 2 hours and then poured into water (500 ml). The mixture was extracted with dichloromethane (3×300 ml) and the combined extracts washed with water (8×200 ml), dried over sodium sulphate and the solvent evaporated under reduced pressure to give a red oil. Purification by flash column chromatography on silica eluting with a 3:7 mixture of ethyl acetate and petroleum ether (b.p. 40–60° C.) gave (R)-5-[2-(2,3-epoxypropoxy)]benzo[b]furan-4-carboxaldehyde (3.11 g) as a yellow solid m.p. 64–65° C.

3-chloroperoxybenzoic acid (85%; 3.88 g) and a solution of trifluroacetic acid (1.61 g) in dichloromethane (5 ml) were added to a stirred solution of the product from the previous reaction (3.08 g) in dichloromethane (40 ml). The mixture was stirred at room temperature for 30 minutes and poured into saturated aqueous sodium bisulphite solution (200 ml) then extracted with dichloromethane (2×150 ml). The combined extracts were washed with saturated aqueous sodium bicarbonate solution (3×150 ml), dried over sodium sulphate and the solvent evaporated under reduced pressure to give (R)-5-[2-(2,3-epoxypropoxy)]benzo[b]furan-4-yl formate (3.10 g) as a red oil.

Saturated aqueous potassium carbonate solution (15 ml) was added to a stirred solution of the product from the previous reaction (3.09 g) in tetrahydrofuran (30 ml) and the mixture stirred vigorously at room temperature for 72 hours. The mixture was poured into water (200 ml) and extracted with ethyl acetate (2×150 ml). The combined extracts were dried over sodium sulphate and the solvent evaporated under reduced pressure to give an orange oil. Purification by flash column chromatography on silica eluting with a 2:3 mixture of ethyl acetate and petroleum ether (b.p. 60–80° C.) gave (S)-2,3-dihydro-2-(hydroxymethyl)furo[3,2-f]-1,4-benzodioxin (1.90 g) as a pale yellow oil.

4-Toluenesulphonyl chloride (1.89 g) was added to a stirred solution of the product from the previous reaction (1.86 g) in dichloromethane (40 ml). 4-Dimethylaminopyridine (1.21 g) was then added and the resulting solution stirred at room temperature for 18 hours. The mixture was diluted with dichloromethane (200 ml) and washed sucessively with water (100 ml), saturated copper sulphate solution (2×100 ml) and water (100 ml). The organic solution was then dried over sodium sulphate and the solvent evaporated under reduced pressure to give (S)-2,3-dihydrofuro[3,2-f]-1,4-benzodioxin-2-ylmethyl 4-toluenesulphonate (3.01 g) as a colourless oil.

A mixture of the product from the previous reaction (2.80 g), potassium carbonate (10.0 g) and 1-[(2-methoxyphenyl) piperid-4-yl]methylamine (1.88 g) in dry acetonitrile (100 ml) was heated under reflux with stirring for 90 hours. The cooled mixture was filtered and the filtrate evaporated under reduced pressure to leave a pale-yellow oil. Purification by flash column chromatography on silica eluting with a 19:1 mixture of dichloromethane and methanol gave a pale-yellow oil which was then dissolved in ethanol (5 ml) and treated with a solution of fumaric acid (0.70 g) in ethanol (5 ml). The solvent was evaporated from the resulting solution under reduced pressure to give (S)-N-(2,3-dihydrofuro[3,2-f]-1,4-benzodioxin-2-ylmethyl)-1-[1-(2-methoxyphenyl) piperid-4-yl]methylamine monofumarate monohydrate (3.06 g) as a pale-yellow solid m.p. 95–6° C., $[\alpha]_D$=−38.5° (C=0.301, MeOH)

EXAMPLE 7

A flask containing a mixture of the product form the previous reaction (1.14 g) and pyridine hydrochloride (10 g) was submerged in a pre-heated oil bath at 180° C. and the resulting solution heated with stirring at 180–200° C. for 2 hours. The cooled reaction mixture was dissolved in water (200 ml), basified with aqueous ammonia, and then extracted with dichloromethane (3×100 ml). The combined extracts were washed with water (100 ml), dried over magnesium sulphate and the solvent evaporated under reduced pressure to leave a brown oil (0.90 g). Purification by flash column chromatography on silica eluting with a 19:1 mixture of dichloromethane and methanol gave a pale orange oil (0.23 g). A portion of this oil (0.2 g) was dissolved in ethanol (1 ml) and then treated with a solution of fumaric acid (60 mg) in ethanol (5 ml). The resulting solution was evaporated under reduced pressure to give (S)-2-{4-[(2,3-Dihydrofuro[3,2-f]-1,4-benzodioxin-2-ylmethyl) aminomethyl]piperidino}phenol monofumarate 1.1 hydrate, 0.25 ethanol solvate (0.27 g) as an orange solid m.p. 88–9° C., $[\alpha]_D$=−37.7° (C=0.257, EtOH)

EXAMPLE 8

A solution of 3,4-methylenedioxyphenol (40 g) in diethyl ether (350 ml) was added dropwise to a stirred suspension of sodium hydride (12.9 g) in a mixture of dimethylformamide (110 ml) and diethyl ether (470 ml) at room temperature. The mixture was stirred until the evolution of hydrogen had ceased, then a solution of diethyl carbamoyl chloride (47 g) in diethyl ether (110 ml) was added and the mixture was stirred for 1 hour, then left to stand at room temperature for 17 hours.

The reaction mixture was poured into water (600 ml) and the product was extracted with diethyl ether (3×300 ml). The ethereal layers were combined, washed with 10% aqueous sodium hydroxide solution (2×200 ml), dried over magnesium sulphate and evaporated under reduced pressure to give 3,4-methylenedioxyphenyl N,N-diethylcarbamate (59 g) as a white solid.

N,N,N',N'-Tetramethylethylenediamine (4 ml) was added to a stirred solution of sec-butyllithium (1.3 M solution in cyclohexane; 21 ml) in tetrahydrofuran (25 ml) at −78° C. The mixture was stirred for 30 minutes then added via a cannula to a stirred solution of the product from the previous reaction (5 g) in tetrahydrofuran (70 ml) at −78° C. The mixture was stirred for 2 hours and then dimethylformamide (10 ml) was added. The reaction mixture was allowed to warm to room temperature over 1 hour and the resulting deep red solution was poured into saturated aqueous ammonium chloride solution (500 ml) and extracted with diethyl ether (3×200 ml). The combined extracts were dried over magnesium sulphate, and the solvent was evaporated under reduced pressure to leave a brown oil. Purification by flash column chromatography on silica eluting with a 9:1 mixture of petroleum ether (b.p. 40–60° C.) and ethyl acetate afforded 5,6-methylenedioxysalicaldehyde (1.1 g) as a yellow solid.

A mixture of potassium carbonate (2.8 g), 5,6-methylenedioxysalicaldehyde, prepared by the method given above, (3.1 g) and (R)-glycidyl tosylate (4.2 g) in dimethylformamide (85 ml) was stirred and heated at 60° C. under an atmosphere of nitrogen for 18 hours. The mixture was poured into water (700 ml) and extracted with diethyl ether (4×300 ml). The combined extracts were washed with brine (3×400 ml), dried over magnesium sulphate and the solvent evaporated under reduced pressure. The yellow solid residue was purified by flash column chromatography on silica eluting with a 2:1 mixture of petroleum ether (b.p. 40–60° C.) and ethyl acetate to give (R)-2-(2,3-epoxypropoxy)-5,6-methylenedioxybenzaldehyde (1.6 g) as a pale yellow solid.

A stirred solution of the product from the previous reaction (1.5 g) and 3-chloroperoxybenzoic acid (56–87%; 4.3 g) in dichloromethane (100 ml) was stirred and heated at reflux temperature for 6.5 hours then left to stand at room temperature for 72 hours. More 3-chloroperoxybenzoic acid (56–87%; 1 g) was then added and the solution was heated for a further 2 hours. The mixture was allowed to cool, washed with saturated aqueous sodium bicarbonate solution (4×400 ml), water (2×400 ml), brine (2×400 ml) and dried over magnesium sulphate. The solvent was evaporated under reduced pressure to afford crude (R)-2-(2,3-epoxypropoxy)-5,6-methylenedioxyphenyl formate (1 g) as a red oil.

Saturated aqueous potassium carbonate solution (13 ml) was added to a solution of the product from the previous reaction (1 g) in tetrahydrofuran (16 ml) and the mixture was stirred at room temperature for 18 hours. The mixture was poured into water (100 ml) and extracted with ethyl acetate (3×60 ml). The combined extracts were dried over magnesium sulphate and the solvent evaporated under reduced pressure to give a brown oil. Purification by flash column chromatography on silica eluting with a 2:1 mixture of petroleum ether (b.p. 40–60° C.) and ethyl acetate afforded (S)-7,8-methylenedioxy-2,3-dihydro-1,4-benzodioxin-2-ylmethanol (0.3 g) as a clear oil.

A solution of 4-toluenesulphonyl chloride (0.29 g) in dichloromethane (10 ml) was added dropwise to a stirred solution of the product from the previous reaction (0.3 g) and 4-dimethylaminopyridine (0.21 g) in dichloromethane (10 ml) at 0–5° C. The mixture was allowed to warm to room temperature and stirred for 18 hours. The solution was diluted with dichloromethane (30 ml) and washed successively with water (100 ml), dilute aqueous hydrochloric acid (5M, 3×100 ml), brine (2×100 ml) and then dried over magnesium sulphate. Evaporation of the solvent under reduced pressure gave (S)-7,8-methylenedioxy-2,3-dihydro-1,4-benzodioxin-2-ylmethyl 4-toluenesulphonate (0.45 g) as a colourless solid.

A mixture of the product from the previous reaction (0.45 g), potassium carbonate (0.32 g) and 1-[1-(2-methoxyphenyl)piperid-4-yl]methylamine (0.51 g) in dimethylformamide (4.5 ml) and toluene (10 ml) was heated at reflux temperature for 6 hours, then left to stand at room temperature for 72 hours and then heated at reflux temperature for a further 4 hours. The cooled mixture was poured into water (300 ml) and extracted with ethyl acetate (3×40 ml). The combined organic extracts were extracted with dilute aqueous hydrochloric acid (5M; 3×30 ml) and the combined aqueous extracts basified by the addition of sodium hydroxide solution (5M). The aqueous phase was extracted with ethyl acetate (3×300 ml), dried over magnesium sulphate and the solvent removed under reduced pressure to yield a yellow oil. Purification by flash column chromatography on silica eluting with a 95:5 mixture of ethyl acetate and methanol afforded (S)-N-(7,8-methylenedioxy-2,3-dihydro-1,4-benzodioxin-2-ylmethyl)-1-[1-(2-methoxyphenyl)piperid-4-yl]methylamine (0.3 g) as a clear oil. Citric acid (0.14 g) in ethanol (20 ml) was added to a solution of the oil in ethanol (20 ml) and the solvent was removed under reduced pressure to afford (S)-N-(7,8-methylenedioxy-2,3-dihydro-1,4-benzodioxin-2-ylmethyl)-1-[1-(2-methoxyphenyl)piperid-4-yl]methyl-amine monocitrate (0.3 g) as a fawn solid; m.p 120–22° C., $[\alpha]_D$–35.9° (c=0.575, MeOH)

EXAMPLE 9

The use of compounds of the present invention in the manufacture of pharmaceutical compositions is illustrated by the following description. In this description the term "active compound" denotes any compound of the invention but particularly any compound which is the final product of one of the preceding Examples.

a) Capsules

In the preparation of capsules, 10 parts by weight of active compound and 240 parts by weight of lactose are de-aggregated and blended. The mixture is filled into hard gelatin capsules, each capsule containing a unit dose or part of a unit dose of active compound.

b) Tablets

Tablets are prepared from the following ingredients.

| | Parts by weight |
|---|---|
| Active compound | 10 |
| Lactose | 190 |
| Maize starch | 22 |
| Polyvinylpyrrolidone | 10 |
| Magnesium stearate | 3 |

The active compound, the lactose and some of the starch are de-aggregated, blended and the resulting mixture is granulated with a solution of the polyvinylpyrrolidone in ethanol. The dry granulate is blended with the magnesium stearate and the rest of the starch. The mixture is then compressed in a tabletting machine to give tablets each containing a unit dose or a part of a unit dose of active compound.

c) Enteric Coated Tablets

Tablets are prepared by the method described in (b) above. The tablets are enteric coated in a conventional manner using a solution of 20% cellulose acetate phthalate and 3% diethyl phthalate in ethanol:dichloromethane (1:1).

d) Suppositories

In the preparation of suppositories, 100 parts by weight of active compound is incorporated in 1300 parts by weight of triglyceride suppository base and the mixture formed into suppositories each containing a therapeutically effective amount of active ingredient.

What is claimed is:

1. A compound of formula I

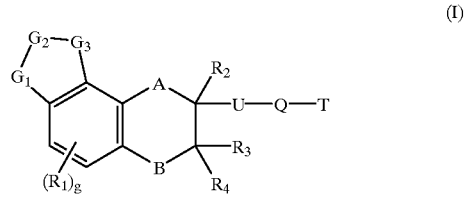

(I)

or a pharmaceutically acceptable salt thereof in the form of an individual enantiomer, a racemate, or another mixture of enantiomers, in which A is methylene or —O—;

B is methylene or —O—;

$G_1$—$G_2$—$G_3$ represent —N(R')—C(R")=C(R''')—, —S—C(R")=C(R''')— or —O—C(R")=C(R''')—, wherein R' is H or an alkyl group containing 1 to 3 carbon atoms; and R" and R''', which are the same or different, are H; halo; an alkyl group containing 1 to 3 carbon atoms optionally substituted by one or more halo; carboxy; an alkanoyl group containing 1 to 6 carbon atoms; an alkoxycarbonyl group in which the alkoxy group contains 1 to 3 carbon atoms; formyl; cyano; or a carbamoyl group or carbamoylmethyl group each optionally N-substituted by one or two alkyl groups, which may be the same or different, each containing 1 to 3 carbon atoms;

g is 0, 1 or 2;

$R_1$ represents an alkyl group containing 1 to 3 carbon atoms optionally substituted by one or more halo; an alkoxy group containing 1 to 3 carbon atoms optionally substituted by one or more halo; halo; or an alkylthio group containing 1 to 3 carbon atoms optionally substituted by one or more halo; the substituents represented by $R_1$ being the same or different when g is 2;

R$_2$ is H or an alkyl group containing 1 to 3 carbon atoms;

R$_3$ and R$_4$, which are the same or different, are H, or an alkyl group containing 1 to 3 carbon atoms;

U is an alkylene chain containing 1 to 3 carbon atoms, optionally substituted by one or more alkyl groups each containing 1 to 3 carbon atoms;

Q represents a divalent group of formula IIa, IIb or IIc

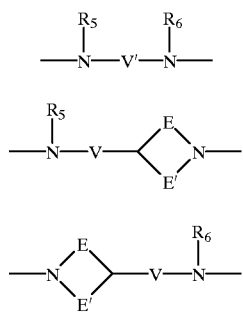

in which V is (CH$_2$)$_n$, wherein n is 0, 1, 2 or 3, optionally substituted by one or more alkyl groups each containing 1 to 3 carbon atoms;

V' is an alkylene chain containing 2 to 6 carbon atoms, optionally substituted by one or more alkyl groups each containing 1 to 3 carbon atoms;

E is an alkylene chain containing 0 to 2 carbon atoms and E' is an alkylene chain containing 1 to 4 carbon atoms provided that the total number of carbon atoms in E and E' amounts to 3 or 4; and R$_5$ and R$_6$, which may be the same or different, are H or an alkyl group containing 1 to 4 carbon atoms; and T represents phenyl, 1- or 2-naphthyl, 1-naphth[2,1-d][1,2,3]oxadiazolyl, 2-, 3- or 4-pyridyl, 2-, 4- or 5-pyrimidinyl, 2- or 3-thienyl, 2- or 3-furyl, 2-, 3- or 7-benzo[b]furanyl, 2,3-dihydro-7-benzo[b]furanyl, 2-, 3- or 7-benzo[b]thiophenyl, 3-, 4- or 5-pyrazolyl, 1,2,3-triazol-4-yl, 1,2,3-triazol-5-yl, 1,2,4-triazol-2-yl, 5-tetrazolyl, 2-, 3- or 4-quinolinyl, 2- or 4-quinazolinyl, 3-, 4- or 5-isoxazolyl, 2-, 4- or 5-oxazolyl, 3-, 4- or 5-isothiazolyl or 2-, 4- or 5-thiazolyl each of which may be optionally substituted by one or more substituents selected from a) halo, b) an alkyl group containing 1 to 4 carbon atoms optionally substituted by one or more halo, c) an alkoxy group containing 1 to 3 carbon atoms optionally substituted by one or more halo, d) an alkylthio group containing 1 to 3 carbon atoms optionally substituted by one or more halo, e) hydroxy, f) an acyloxy group containing 1 to 3 carbon atoms, g) hydroxymethyl, h) cyano, i) an alkanoyl group containing 1 to 6 carbon atoms, j) an alkoxycarbonyl group containing 2 to 6 carbon atoms, k) a carbamoyl group or carbamoylmethyl group each optionally N-substituted by one or two alkyl groups each containing 1 to 3 carbon atoms, l) a sulphamoyl or sulphamoylmethyl group each optionally N-substituted by one or two alkyl groups each containing 1 to 3 carbon atoms, m) an amino group optionally substituted by one or two alkyl groups each containing 1 to 5 carbon atoms, n) 1-pyrrolidinyl or 1-piperidinyl, o) nitro or p) acetamido.

2. The compound defined in claim 1 in which both A and B are —O—.

3. The compound defined in claim 1 in which g is 0 or 1.

4. The compound defined in claim 1 in which R$_1$ is halo or an alkyl group containing 1 to 3 carbon atoms.

5. The compound defined in claim 1 in which G$_1$—G$_2$—G$_3$ are —N(R')—C(R'')=C(R''')— or —S—C(R'')=C(R''')—.

6. The compound defined in claim 1 in which R$_2$ is H.

7. The compound defined in claim 1 in which R$_3$ and R$_4$, are both H.

8. The compound defined in claim 1 in which U is methylene.

9. The compound defined in claim 1 in which Q is a group of formula IIa in which V is methylene, E and E' are both ethylene and R$_5$ is H.

10. The compound defined in claim 1 in which T is phenyl or naphthyl, each of which may be optionally substituted by one or more substituents selected from an alkoxy group containing 1 to 3 carbon atoms, hydroxy, or halo.

11. The compound defined in claim 1 in which G$_1$—G$_2$—G$_3$ are —O—CH=CH—.

12. The compound of formula I, defined in claim 1, selected from:
N-(9-Chloro-2,3-dihydrothieno[3,2-f]-1,4-benzodioxin-2-ylmethyl)-1-[1-(2-methoxyphenyl)piperid-4-yl]methylamine;
N-(2,3-Dihydrothieno[3,2-f]-1,4-benzodioxin-2-ylmethyl)-1-[1-(2-methoxyphenyl)piperid-4-yl]methylamine;
Ethyl 2,3-dihydro-2-(N-{[1-(2-methoxyphenyl)piperid-4-yl]methyl}aminomethyl)-7H-1,4-dioxino[2,3-e]indole-8-carboxylate;
N-(2,3-Dihydro-7H-1,4-dioxino[2,3-e]indol-2-ylmethyl)-1-[1-(2-methoxyphenyl)piperid-4-yl]methylamine;
N-(2,3-Dihydro-7H-1,4-dioxino[2,3-e]indazol-2-ylmethyl)-1-[1-(2-methoxyphenyl)piperid-4-yl]methylamine;
N-(2,3-Dihydrofuro[3,2-f]-1,4-benzodioxin-2-ylmethyl)-1-[1-(2-methoxyphenyl)piperid-4-yl]methylamine;
2-{4-[(2,3-Dihydrofuro[3,2-f]-1,4-benzodioxin-2-ylmethyl)aminomethyl]piperidino}-phenol;
and a pharmaceutically acceptable salt thereof in the form of an individual enantiomer, a racemate, or another mixture of enantiomers.

13. A compound of formula I defined in claim 1 selected from
(S)-N-(9-Chloro-2,3-dihydrothieno[3,2-f]-1,4-benzodioxin-2-ylmethyl)-1-[1-(2-methoxyphenyl)piperid-4-yl]methylamine;
(S)-N-(2,3-Dihydrothieno[3,2-f]-1,4-benzodioxin-2-ylmethyl)-1-[1-(2-methoxyphenyl)piperid-4-yl]methylamine;
Ethyl (S)-2,3-dihydro-2-(N-{[1-(2-methoxyphenyl)piperid-4-yl]methyl}aminomethyl)-7H-1,4-dioxino[2,3-e]indole-8-carboxylate;
(S)-N-(2,3-Dihydro-7H-1,4-dioxino[2,3-e]indol-2-ylmethyl)-1-[1-(2-methoxyphenyl)-piperid-4-yl]methylamine;
(S)-N-(2,3-Dihydro-7H-1,4-dioxino[2,3-e]indazol-2-ylmethyl)-1-[1-(2-methoxyphenyl)piperid-4-yl]methylamine;
(S)-N-(2,3-Dihydrofuro[3,2-f]-1,4-benzodioxin-2-ylmethyl)-1-[1-(2-methoxyphenyl)piperid-4-yl]methylamine;
(S)-2-{4-[(2,3-Dihydrofuro[3,2-f]-1,4-benzodioxin-2-ylmethyl)aminomethyl]-piperidino}phenol;
and a pharmaceutically acceptable salt thereof.

14. A pharmaceutical composition comprising the compound of formula I defined in claim 1, in conjunction with a pharmaceutically acceptable diluent or carrier.

15. The compound of formula I defined in claim 1, for use as a medicament.

16. The composition defined in claim 14 for use in the treatment of depression, anxiety, psychoses, tardive dyskinesia, Parkinson's disease, obesity, hypertension, Tourette's syndrome, sexual dysfunction, drug addiction, drug abuse, cognitive disorders, Alzheimer's disease, senile dementia, obsessive-compulsive behaviour, panic attacks, social phobias, eating disorders, anorexia, cardiovascular and cerebrovascular disorders, non-insulin dependent diabetes mellitus, hyperglycaemia, constipation, arrhythmia, disorders of the neuroendocrine system, stress, and spasticity.

17. The composition defined in claim 16, for use in the treatment of psychoses.

18. Use of a compound of formula I, as claimed in claim 1, in the manufacture of a medicament for treating depression, anxiety, psychoses, tardive dyskinesia, Parkinson's disease, obesity, hypertension, Tourette's syndrome, sexual dysfunction, drug addiction, drug abuse, cognitive disorders, Alzheimer's disease, senile dementia, obsessive-compulsive behaviour, panic attacks, social phobias, eating disorders and anorexia, cardiovascular and cerebrovascular disorders, non-insulin dependent diabetes mellitus, hyperglycaemia, constipation, arrhythmia, disorders of the neuroendocrine system, stress, or spasticity.

19. A method of treating depression, anxiety, psychoses, tardive dyskinesia, Parkinson's disease, obesity, hypertension, Tourette's syndrome, sexual dysfunction, drug addiction, drug abuse, cognitive disorders, Alzheimer's disease, senile dementia, obsessive-compulsive behaviour, panic attacks, social phobias, eating disorders and anorexia, cardiovascular and cerebrovascular disorders, non-insulin dependent diabetes mellitus, hyperglycaemia, constipation, arrhythmia, disorders of the neuroendocrine system, stress, or spasticity in human beings, which comprises the administration of a therapeutically effective amount of a compound of formula I, as claimed in claim 1, to a patient in need thereof.

20. A process for the preparation of compounds of formula I, as claimed in claim 1, in which Q is a group of formula IIa, comprising the reaction of a compound of formula III

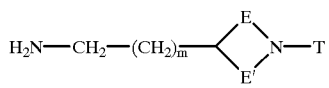

in which m is 0, 1 or 2, with a compound of formula IV

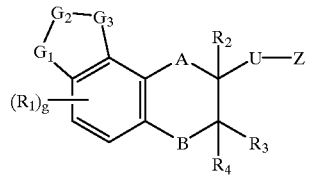

in which Z is a leaving group, optionally in the presence of a base, and optionally in a solvent.

21. A compound of formula I

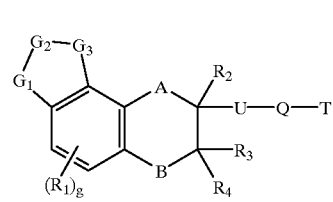

or a pharmaceutically acceptable salt thereof in the form of an individual enantiomer, a racemate, or another mixture of enantiomers, in which A is methylene or —O—;
B is methylene or —O—;
$G_1$—$G_2$—$G_3$ represent —N(R')—C(R")=N—, —N=C(R")—N(R')—, —N(R')—C(R")=C(R''')—, —C(R")=C(R")—N(R')—, —N(R')—N=C(R")—, —C(R")=N—N(R')—, —N(R')—N=N—, —N=N—N(R')—, wherein
R' is H or an alkyl group containing 1 to 3 carbon atoms; and
R" and R''', which are the same or different, are H; halo; an alkyl group containing 1 to 3 carbon atoms optionally substituted by one or more halo; carboxy; an alkanoyl group containing 1 to 6 carbon atoms; an alkoxycarbonyl group in which the alkoxy group contains 1 to 3 carbon atoms; formyl; cyano; or a carbamoyl group or carbamoylmethyl group each optionally N-substituted by one or two alkyl groups, which may be the same or different, each containing 1 to 3 carbon atoms;

g is 0, 1 or 2;
$R_1$ represents an alkyl group containing 1 to 3 carbon atoms optionally substituted by one or more halo; an alkoxy group containing 1 to 3 carbon atoms optionally substituted by one or more halo; halo; or an alkylthio group containing 1 to 3 carbon atoms optionally substituted by one or more halo; the substituents represented by $R_1$ being the same or different when g is 2;
$R_2$ is H or an alkyl group containing 1 to 3 carbon atoms;
$R_3$ and $R_4$, which are the same or different, are H, or an alkyl group containing 1 to 3 carbon atoms;
U is an alkylene chain containing 1 to 3 carbon atoms, optionally substituted by one or more alkyl groups each containing 1 to 3 carbon atoms;
Q represents a divalent group of formula IIa, IIb or IIc

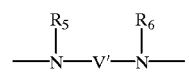

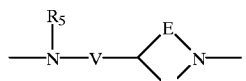

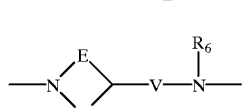

in which V is $(CH_2)_n$, wherein n is 0, 1, 2 or 3, optionally substituted by one or more alkyl groups each containing 1 to 3 carbon atoms;

V' is an alkylene chain containing 2 to 6 carbon atoms, optionally substituted by one or more alkyl groups each containing 1 to 3 carbon atoms;

E is an alkylene chain containing 0 to 2 carbon atoms and E' is an alkylene chain containing 1 to 4 carbon atoms provided that the total number of carbon atoms in E and E' amounts to 3 or 4; and $R_5$ and $R_6$, which may be the same or different, are H or an alkyl group containing 1 to 4 carbon atoms; and T represents phenyl, 1- or 2-naphthyl, 1-naphth[2,1-d][1,2,3]oxadiazolyl, 2-, 3- or 4-pyridyl, 2-, 4- or 5-pyrimidinyl, 2- or 3-thienyl, 2- or 3-furyl, 2-, 3- or 7-benzo[b]furanyl, 2,3-dihydro-7-benzo[b]furanyl, 2-, 3- or 7-benzo[b]thiophenyl, 3-, 4- or 5-pyrazolyl, 1,2,3-triazol-4-yl, 1,2,3-triazol-5-yl, 1,2,4-triazol-2-yl, 5-tetrazolyl, 2-, 3- or 4-quinolinyl, 2- or 4-quinazolinyl, 3-, 4- or 5-isoxazolyl, 2-, 4- or 5-oxazolyl, 3-, 4- or 5-isothiazolyl or 2-, 4- or 5-thiazolyl each of which may be optionally substituted by one or more substituents selected from a) halo, b) an alkyl group containing 1 to 4 carbon atoms optionally substituted by one or more halo, c) an alkoxy group containing 1 to 3 carbon atoms optionally substituted by one or more halo, d) an alkylthio group containing 1 to 3 carbon atoms optionally substituted by one or more halo, e) hydroxy, f) an acyloxy group containing 1 to 3 carbon atoms, g) hydroxymethyl, h) cyano, i) an alkanoyl group containing 1 to 6 carbon atoms, j) an alkoxycarbonyl group containing 2 to 6 carbon atoms, k) a carbamoyl group or carbamoylmethyl group each optionally N-substituted by one or two alkyl groups each containing 1 to 3 carbon atoms, l) a sulphamoyl or sulphamoylmethyl group each optionally N-substituted by one or two alkyl groups each containing 1 to 3 carbon atoms, m) an amino group optionally substituted by one or two alkyl groups each containing 1 to 5 carbon atoms, n) 1-pyrrolidinyl or 1-piperidinyl, o) nitro or p) acetamido.

\* \* \* \* \*